(12) United States Patent
Cox et al.

(10) Patent No.: US 9,115,349 B2
(45) Date of Patent: Aug. 25, 2015

(54) HYDROPHOBIN SOLUTION CONTAINING ANTIFOAM

(75) Inventors: Andrew Richard Cox, Sharnbrook (GB); Andrew Baxter Russell, Sharnbrook (GB); Christopher Mark Tier, Sharnbrook (GB)

(73) Assignee: Conopco, Inc., Englewood Cliffs, NJ (US)

( * ) Notice: Subject to any disclaimer, the term of this patent is extended or adjusted under 35 U.S.C. 154(b) by 964 days.

(21) Appl. No.: 12/578,752

(22) Filed: Oct. 14, 2009

(65) Prior Publication Data

US 2010/0099844 A1 Apr. 22, 2010

(30) Foreign Application Priority Data

Oct. 16, 2008 (WO) .................. PCT/EP2008/063929

(51) Int. Cl.
  *A61K 38/00* (2006.01)
  *C07K 16/00* (2006.01)
  *C12N 1/34* (2006.01)
  *C07K 14/37* (2006.01)
  *C12P 21/02* (2006.01)

(52) U.S. Cl.
  CPC . *C12N 1/34* (2013.01); *C07K 14/37* (2013.01); *C12P 21/02* (2013.01)

(58) Field of Classification Search
  None
  See application file for complete search history.

(56) References Cited

U.S. PATENT DOCUMENTS

| | | | |
|---|---|---|---|
| 2,604,406 A | 7/1952 | Bilhovde | |
| 2,844,470 A | 7/1958 | Akerboom et al. | |
| 2,937,093 A | 5/1960 | Gorman et al. | |
| 2,970,917 A | 2/1961 | Melnick | |
| 3,266,214 A | 8/1966 | Kramme | |
| 3,346,387 A | 10/1967 | Moncrieff et al. | |
| 3,914,441 A | 10/1975 | Finney et al. | |
| 3,946,122 A | 3/1976 | Scharp | |
| 4,012,533 A | 3/1977 | Jonas | |
| 4,066,794 A | 1/1978 | Schur | |
| 4,146,652 A | 3/1979 | Kahn et al. | |
| 4,244,982 A | 1/1981 | Menzi et al. | |
| 4,305,964 A | 12/1981 | Moran et al. | |
| 4,325,980 A | 4/1982 | Rek et al. | |
| 4,425,369 A | 1/1984 | Sakamoto et al. | |
| 4,542,035 A | 9/1985 | Huang et al. | |
| 4,627,983 A | 12/1986 | Scharf et al. | |
| 4,629,628 A | 12/1986 | Negro | |
| 4,668,519 A | 5/1987 | Dartey et al. | |
| 4,869,915 A | 9/1989 | Inayoshi et al. | |
| 4,874,627 A | 10/1989 | Greig et al. | |
| 4,931,397 A | 6/1990 | Montgomery et al. | |
| 4,946,625 A | 8/1990 | O'Lenick | |
| 4,954,410 A | 9/1990 | Takuma et al. | |
| 4,960,540 A | 10/1990 | Friel et al. | |
| 5,084,295 A | 1/1992 | Whelan | |
| 5,104,674 A | 4/1992 | Chen et al. | |
| 5,202,147 A | 4/1993 | Traska et al. | |
| 5,208,028 A | 5/1993 | Clement et al. | |
| 5,215,777 A | 6/1993 | Asher et al. | |
| 5,336,514 A | 8/1994 | Jones et al. | |
| 5,393,549 A | 2/1995 | Badertscher et al. | |
| 5,397,592 A | 3/1995 | Vermaas et al. | |
| 5,436,021 A | 7/1995 | Bodor et al. | |
| 5,486,372 A | 1/1996 | Martin et al. | |
| 5,486,732 A | 1/1996 | Rondier | |
| 5,536,514 A | 7/1996 | Bishay et al. | |
| 5,624,612 A | 4/1997 | Sewall et al. | |
| 5,681,505 A | 10/1997 | Phillips et al. | |
| 5,738,897 A | 4/1998 | Gidley et al. | |
| 5,770,248 A | 6/1998 | Leibfred et al. | |
| 5,780,092 A | 7/1998 | Agbo et al. | |
| 5,809,787 A | 9/1998 | Zittel | |
| 5,925,394 A | 7/1999 | Levinson | |
| 5,980,969 A | 11/1999 | Mordini et al. | |
| 6,063,602 A | 5/2000 | Prosperi et al. | |
| 6,096,867 A | 8/2000 | Byass et al. | |
| 6,187,365 B1 | 2/2001 | Vaghela et al. | |
| 6,238,714 B1 | 5/2001 | Binder et al. | |
| 6,245,957 B1 | 6/2001 | Wagner et al. | |
| 6,284,303 B1 | 9/2001 | Rowe et al. | |
| 6,497,913 B1 | 12/2002 | Gray et al. | |
| 6,685,977 B1 | 2/2004 | Asano et al. | |
| 6,914,043 B1 | 7/2005 | Chapman et al. | |
| 7,338,779 B1 * | 3/2008 | Nakari-Setala et al. | ........ 435/42 |
| 8,038,740 B2 * | 10/2011 | Subkowski et al. | ............. 44/300 |
| 8,206,770 B2 | 6/2012 | Aldred et al. | |
| 8,216,624 B2 | 7/2012 | Berry et al. | |
| 8,354,503 B2 | 1/2013 | Hedges | |
| 8,357,420 B2 | 1/2013 | Cox et al. | |

(Continued)

FOREIGN PATENT DOCUMENTS

| | | |
|---|---|---|
| CA | 2575325 | 2/2006 |
| CN | 101054407 | 10/2007 |

(Continued)

OTHER PUBLICATIONS

Linder et al. ( FEMS Microbiology, Reviews, vol. 29, pp. 877-896, 2005).*
Woesten, "Hydrophobins, the fungal coat unravelled", Biochimica et Biophysica Scta. MR. Reviews on Biomembranes, Elsevier, Amsterdam, NL, vol. 1469, No. 2, Sep. 2000, pp. 79-86.
Wosten, "Hydrophobins: Multipurpose Proteins", 2001, Annu. Rev. Microbiol. 55: pp. 625-646.

(Continued)

*Primary Examiner* — Gary Nickol
*Assistant Examiner* — Khatol Shahnan Shah
(74) *Attorney, Agent, or Firm* — Alan A. Bornstein

(57) ABSTRACT

Aqueous solution containing at least 300 mg/l of hydrophobin and at least 0.3 mg/l of antifoam, wherein the antifoam/hydrophobin weight ratio is below 0.2, preferably below 0.15, more preferably below 0.1.

9 Claims, No Drawings

(56) References Cited

U.S. PATENT DOCUMENTS

| | | |
|---|---|---|
| 8,394,444 B2 | 3/2013 | Cox et al. |
| 8,647,696 B2 | 2/2014 | Norton et al. |
| 2001/0048962 A1 | 12/2001 | Fenn et al. |
| 2002/0085987 A1 | 7/2002 | Brown et al. |
| 2002/0155208 A1 | 10/2002 | Benjamins et al. |
| 2002/0165114 A1 | 11/2002 | Fowler et al. |
| 2002/0182300 A1 | 12/2002 | Groh et al. |
| 2002/0197375 A1 | 12/2002 | Adolphi et al. |
| 2003/0087017 A1 | 5/2003 | Hanselmann et al. |
| 2003/0099751 A1 | 5/2003 | Aldred et al. |
| 2003/0134025 A1 | 7/2003 | Vaghela et al. |
| 2003/0148400 A1 | 8/2003 | Haikara et al. |
| 2003/0166960 A1 | 9/2003 | DeVocht et al. |
| 2003/0175407 A1 | 9/2003 | Kunst et al. |
| 2003/0190402 A1 | 10/2003 | McBride |
| 2004/0109930 A1 | 6/2004 | Hooft et al. |
| 2004/0185162 A1 | 9/2004 | Finnigan et al. |
| 2005/0037000 A1 | 2/2005 | Stavenhagen et al. |
| 2005/0037110 A1 | 2/2005 | Windhab et al. |
| 2005/0123666 A1 | 6/2005 | Vaghela et al. |
| 2005/0123668 A1 | 6/2005 | Kodali et al. |
| 2005/0129810 A1 | 6/2005 | Lindner et al. |
| 2005/0193744 A1 | 9/2005 | Cockings et al. |
| 2005/0220961 A1 | 10/2005 | Cox et al. |
| 2005/0272646 A1 | 12/2005 | Koteva et al. |
| 2006/0024417 A1 | 2/2006 | Berry et al. |
| 2006/0024419 A1 | 2/2006 | Aldred et al. |
| 2007/0014906 A1 | 1/2007 | Leon |
| 2007/0071865 A1 | 3/2007 | Aldred et al. |
| 2007/0116848 A1 | 5/2007 | Aldred et al. |
| 2007/0286936 A1 | 12/2007 | Bramley et al. |
| 2007/0298490 A1 | 12/2007 | Sweigard et al. |
| 2008/0187633 A1 | 8/2008 | Cox |
| 2008/0254180 A1 | 10/2008 | Windhab et al. |
| 2008/0305237 A1 | 12/2008 | Beltman et al. |
| 2009/0136433 A1 | 5/2009 | Subkowski et al. |
| 2009/0162344 A1 | 6/2009 | Soma et al. |
| 2010/0112179 A1 | 5/2010 | Cox et al. |
| 2010/0184875 A1 | 7/2010 | Bezemer et al. |
| 2010/0273983 A1 | 10/2010 | Kaar et al. |
| 2010/0303987 A1 | 12/2010 | Watts et al. |
| 2011/0020402 A1 | 1/2011 | Meinke et al. |
| 2011/0287150 A1 | 11/2011 | Norton et al. |
| 2012/0064201 A1 | 3/2012 | Nafisi-Movaghar et al. |
| 2012/0070560 A1 | 3/2012 | Kurokawa |
| 2012/0128858 A1 | 5/2012 | Aldred et al. |
| 2013/0260007 A1 | 10/2013 | Aldred et al. |

FOREIGN PATENT DOCUMENTS

| | | |
|---|---|---|
| CN | 101215321 | 7/2008 |
| EP | 216270 | 4/1987 |
| EP | 0285198 | 10/1988 |
| EP | 0322952 A2 | 7/1989 |
| EP | 0469656 | 2/1992 |
| EP | 0477825 B1 | 12/1996 |
| EP | 747301 | 12/1996 |
| EP | 0775444 A1 | 5/1997 |
| EP | 1074181 A1 | 2/2001 |
| EP | 0771531 B1 | 9/2002 |
| EP | 1153084 | 9/2002 |
| EP | 1284106 | 2/2003 |
| EP | 1327390 | 7/2003 |
| EP | 1402790 | 5/2004 |
| EP | 1849461 A1 | 10/2007 |
| GB | 459583 | 1/1937 |
| GB | 1233258 | 5/1971 |
| GB | 2134117 | 5/1986 |
| JP | 530006491 | 1/1978 |
| JP | 59017946 | 1/1984 |
| JP | 61219342 | 9/1986 |
| JP | 61293348 | 12/1986 |
| JP | 03164156 | 7/1991 |
| JP | 3244348 A | 10/1991 |
| JP | 5503426 | 6/1993 |
| JP | 08500486 | 1/1996 |
| JP | 8503608 | 4/1996 |
| JP | 2002508303 | 12/1998 |
| JP | 2001136905 | 5/2001 |
| JP | 2002218907 A | 8/2002 |
| JP | 200573612 | 3/2005 |
| JP | 2005073612 | 3/2005 |
| JP | 2005176738 | 7/2005 |
| JP | 2005278484 | 10/2005 |
| JP | 2002218907 | 8/2006 |
| JP | 2007202417 | 8/2007 |
| JP | 2007202417 A | 8/2007 |
| JP | 2008000061 | 1/2008 |
| JP | 2012512302 | 5/2012 |
| WO | WO9013571 | 11/1990 |
| WO | WO9222581 | 12/1992 |
| WO | WO9403617 | 2/1994 |
| WO | WO 94/13154 | 6/1994 |
| WO | WO9412050 | 6/1994 |
| WO | WO9523843 | 9/1995 |
| WO | WO9611586 | 4/1996 |
| WO | WO9621362 | 7/1996 |
| WO | WO9804699 | 2/1998 |
| WO | WO9937673 | 7/1999 |
| WO | WO 01/14521 | 3/2001 |
| WO | WO0135756 A1 | 5/2001 |
| WO | WO 01/74864 | 10/2001 |
| WO | WO0184945 A1 | 11/2001 |
| WO | WO03015530 A1 | 2/2003 |
| WO | WO03051136 A1 | 6/2003 |
| WO | WO03053883 | 7/2003 |
| WO | WO 01/096821 | 11/2003 |
| WO | WO2005036976 | 4/2005 |
| WO | WO2005058067 A1 | 6/2005 |
| WO | WO 2005/113387 | 12/2005 |
| WO | WO2007008560 | 1/2007 |
| WO | WO2008031796 A1 | 3/2008 |
| WO | WO2008046729 | 4/2008 |
| WO | WO2008116715 | 10/2008 |
| WO | WO 2009/047657 | 4/2009 |
| WO | WO2010067059 A1 | 6/2010 |
| WO | WO2010136355 | 12/2010 |

OTHER PUBLICATIONS

Co-pending application for Berry et al., U.S. Appl. No. 11/168,209, filed Jun. 27, 2005.
Co-pending application for Aldred et al., U.S. Appl. No. 11/168,214, filed Jun. 27, 2005.
Co-pending application for Aldred et al., U.S. Appl. No. 11/524,977, filed Sep. 21, 2006.
Co-pending application for Aldred et al., U.S. Appl. No. 11/525,060, filed Sep. 26, 2006.
Co-pending application for Cox et al., U.S. Appl. No. 11/524,675, filed Sep. 21, 2006.
Co-pending application for Bramley, et al., U.S. Appl. No. 11/639,851, filed Dec. 12, 2006.
Co-pending application for Cox, et al., U.S. Appl. No. 11/699,601, filed Jan. 30, 2007.
Co-pending application for Cox, et al., U.S. Appl. No. 11/699,602, filed Jan. 30, 2007.
Co-pending application for Burmester, et al., U.S. Appl. No. 12/002,684, filed Dec. 18, 2007.
Co-pending application for Cox, et al., U.S. Appl. No. 12/682,717, filed Apr. 12, 2010.
Co-pending application for Aldred, et al., U.S. Appl. No. 12/287,957, filed Oct. 15, 2008.
Co-pending application for Cox, et al., U.S. Appl. No. 12/578,752, filed Oct. 14, 2009.
Co-pending application for Aldred et al., U.S. Appl. No. 12/788,395, filed May 27, 2010.
Co-pending application for Walts, et al., U.S. Appl. No. 12/786,419, filed May 27, 2010.
Co-pending application for Bialek, et al., U.S. Appl. No. 11/643,586, filed Dec. 21, 2008.
Co-pending application for Cox, et al., U.S. Appl. No. 12/532,667, filed Sep. 23, 2009.

(56) References Cited

OTHER PUBLICATIONS

Co-pending application for Cox, et al., U.S. Appl. No. 12/532,670, filed Sep. 23, 2009.
Co-pending application for Cox, et al., U.S. Appl. No. 12/780,294, filed May 14, 2010.
Co-pending application for Cox, et al., U.S. Appl. No. 12/780,323, filed May 14, 2010.
Co-pending application for Hedges, et al., U.S. Appl. No. 636,157, filed Dec. 11, 2009.
Co-pending application for Aurnaitre, et al., U.S. Appl. No. 12/409,549, filed Mar. 24, 2009.
2012, West Search History for U.S. Appl. No. 12/636,157, Carbohydrates, pp. 1-29.
Joseph M. Light, 1990, Modified Food Starches Why What Where and How, Modified Food Starches, vol. 35, No. 11, pp. 1-20.
Pardun, 1977, Soy Protein Preparations as Antispattering Agents for Margarine, Fette Seifen Anstrichmittel, vol. 79, No. 5, pp. 195-203.
Patino and Pilosof, 2011, Protein-polysaccharide interactions at fluid interfaces, Food Hydrocolloids, 25, 1925-1937.
Penttila, et al., Jan. 1, 2004, Molecular Biology of Trichoderma & Biotechnological Applications, Handbook of Fungal Biotech, 2nd Ed, 413-427.
Quintas, et al., Jan. 1, 2006, Rheology of superstaurated sucrose solutions, Journal of Food Engineering, 77, pp. 844-852.
Samsudin, May 26, 20106, Low-Fat Chocolate Spread Based on Palm Oil, Malasyian Palm Oil Board, pp. 27-30.
Sanderson, 1981, Applications of Xanthan Gum, British Polymer Jr., 13, 71-75.
Schmitt, Feb. 27, 2012, Declaration of Christophe Schmitt, Declaration of Christophe Schmitt, 1-4.
Scott et al., 1983, Influence of Temperature on the Measurement of Water Activity of Food and Salt Systems, Journal of Food Science, vol. 48, pp. 552-554.
Sienkiewicz, Jan. 1, 1990, Whey and Whey Utilization, Verlag Th Mann, 2nd Ed, 82-83.
Soukoulis, et al, May 2, 2008, Impact of the acidification process hydrocolloids & protein fortifiers on the physical & Sensory properties of frozen yogurt, Intl Journal of Dairy Tech, 61, No. 2, 170-177.
Swern, Jan. 1, 1979, Baileys Industrial Oil and Fat Products, John Wiley & Sons, 1, 369.
Takai, et al., Jan. 1, 1978, Cerato-ulmin, a wilting toxin of ceratocystis ulmi: isolation & some properties of cerato-ulmin from the culture of *C. ulmi*, Phytopath, 91, 129-146.
Talbot, Sep. 16, 2003, Aerial Morphogenesis Enter the Chaplins, Current Biology, 13, R696-R698.
Talbot, et al., Jun. 1, 1996, MPG1 encodes a fungal hydrophobin involved in surface interactions during infection-related develop of magnaporthe grisea, Plant Cell, 8, 985-999.
Tchuenbou-Magaia, et al., Mar. 16, 2009, Hydrophobins stabilised air-filled emulsions for the food industry, Food Hydrocolloids, 23, 1877-1885.
Temple, 2000, Biological Roles for cerato-Ulmin, a Hydrophobin secreted by the elm pathogens, *Opthiostoma ulmi* and *O. novo-ulmi*, Micological Society of America, 92, pp. 2-3 (abstract only).
Wang et al, May 31, 2004, Protease a Stability of Beer Foam II, China Academic Journal Electronic Publishing House, ., 11-15.
Whitcomb, et al., Jan. 1, 1980, Rheology of Guar Solutions, Journal of Applied Polymer Sc, 25, 2815-2827.
Wosten, et al., Jan. 1, 1994, Interfacial self-assembly of a hydrophobin into an amphipathic protein membrane mediates fungal attachment to hydrophobic surfaces, EMBO Journal, 13, 5848-5854.
Wosten, et al., Nov. 1, 1993, Interfacial self-assembly of a fungal hydrophobin into a hydrophobic rodlet layer, Plant Cell, 5, 1567-1574.
Co-pending application Aldred et al., U.S. Appl. No. 13/378,143, filed Feb. 10, 2012.
Co-pending application Hedges et al., U.S. Appl. No. 12/636,157, filed Dec. 11, 2009.
Co-pending application Mitchell et al., U.S. Appl. No. 13/498,157, filed Mar. 26, 2012.

Askolin, S., Characterization of the Trichoderma resel hydrophobins HFBI and HFBII, VTT Publication 601, May 2006, 1-99 ; I1-I19; VI1-VI20.
Celus, Fractionation and Characterization of Brewer's Spent Grain Protein Hydrolysates, Journal of Agricultural and Food Chemistry, May 20, 2009, 5563-5570, 57, BE.
Dusane et al., Disruption of *Yarrowia lipolytica* biofilms by rhamnolipid biosurfactant, Aquatic Biosystems, 2012, pp. 1-7, vol. 8, No. 7.
Eliassi et al., Determination of Cloud Points of Poly (propylene glycol) Aqueous Mixtures Using Particle Counting Method, A Chemical Industries Research Dept., 2006, pp. 1-7.
Huang, Sidai, Flour protein structure and functionality in baked products, Grain Storage, The countermove of controlling the resistance of insects to insecticide in warehouse, Dec. 31, 1988, 25-30, 17, CN.
Jackson, Hard or Soft, red or White—or a blend?, Flour Power, Apr. 16, 2008, pp. 1-4.
Co-Pending application Cox et al., U.S. Appl. No. 13/585,257, filed Aug. 14, 2012.
Co-pending application Deborah Lynner Aldred et al., U.S. Appl. No. 13/989,820, filed May 28, 2013, pp. 1-11.
Co-pending application Cox, U.S. Appl. No. 13/878,491, filed Apr. 9, 2013, pp. 1-20.
Co-pending application Deborah Lynne Aldred et al., U.S. Appl. No. 13/992,299, filed Jun. 7, 2013.
Anonymous, List of Cookies, Wikipedia, 2014, pp. 1-12http://en.wikipedia.org/wiki/List_of_cookies.
Glaser et al, Foaming behavior of mixed bovine serum albumin protamine systems, Food Hydrocolloids Elsevier, May 22, 2006, 495-506, vol. 21.
Hafnar et al, Development and in Vitro Characterization of Chitosan based Microspheres ofr Nasal Delivery of Promethazine, DDIP Abstract, 2007, 427, vol. 33—No. 4.
Igoe et al., Dictionary of Food Ingredients, Dictionary of Food Ingredients 3rd Edition pp. 6, 69, 70 and 84 Chapman and Hall 1996, 1996, 6, 69, 70 and 84, .., Chapman & Hall, ., US.
IPRP2 in PCTEP2013050473, Jun. 27, 2014.
Martinac etal, Development and bioadhesive properties of chitosan ethylcellulose microspheres for nasal delivery, Int J Pharmac Abstract, Mar. 3, 2005, p. 69-77, vol. 291—No. 1-2.
Search Report in EP12152824, Jul. 23, 2012.
Search report in PCTEP2013050473, Mar. 14, 2013.
Srinivasan Damodaran, Protein Stabilization of Emulsions and Foams, Journal of Food Science, Mar. 22, 2005, 54-66, vol. 70—No. 3.
Tchuenbou-Magaia et al, Tribological study of suspensions of cysteine-rich protein stabilized microbubbles and subsequent triphasic A/O/W emulsions, Journal of Texture Studies, 2011, 185-196, vol. 42.
Wang et al, Mechanisms of Protein Adhesion on Surface Films of Hydrophobin, Langmuir American Chemical Society, Apr. 23, 2010, 8491-8496, vol. 26—No. 11.
Wang, Coalescence and disproportionation of air bubbles stabilized by proteins and emulsion droplets, School of Food Science and Nutrition, Nov. 2008, 1-187.
Written Opinion in EP12152824, Jul. 23, 2012.
Co-pending application Kuil et al., U.S. Appl. No. 14/373,428, filed Jul. 21, 2014.
Jan. 1, 2005, Fats Oils Fatty Acids Triglycerides, Scientific Psychic, 1-4.
Jun. 14, 2010, Guar Gum, Guargum.biz, 1.
Oct. 16, 2009, Search proteins matching the sequence pattern used for the hydrophobin definition in patent EP 1926 399 B1, Nestle Research Center, 1-3.
Feb. 25, 2008, Research pushes the right buttons, mushrooms are the new fat, University of Birmingham, 1-2.
Arbuckle, 1972, Ice Cream, Ice Cream, 2nd Edition, pp. 15, 18, 31, 35, 61, 65, 265-266, 284-285.
Akari-Setala, et al., May 26, 1997, Differential expression of the vegetative and spore-bound hydrophobins of Trichoderma reesei, Eur J. Biochem, 248, 415-423.

(56) References Cited

OTHER PUBLICATIONS

Murray, Aug. 3, 2007, Stabilization of bubbles and foams, Current Opinion in Colloid & Interface Science, 12, 232-241.
Miquelim et al., 2010, pH Influence on the stability of foams with protein-polysaccharide complexes at their interfaces, Food Hydrocolloids, 24, No. 4, 398-405.
Minor, et al., Jan. 1, 2009, Preparation and sensory perception of fat-free foams effect of matrix properties and level of aeration, Intl Journ of Food Sc & Tech, 44, 735-747.
Askolin, et al., Jan. 10, 2006, Interaction & comparison of a Class I Hydrophobin from schizophyllum commune & Class II Hydro form trichoderma reesei, Biomacromolecules, 7, 1295-1301.
Bailey, et al., Jan. 31, 2002, Process Technol effects of deletion & amplification of hydrophobins I & II in transformants of *Trich reesei*, Appl Microbiol Biotechnol, 58, 721-727.
Bay, Jan. 1, 2002, La Cucina Italiana Italian Cuisine, Edizioni Piemme, 1233.
Berolzheimer, Jan. 1, 1988, Culinary Arts Institute Encyclopedic Cookbook, Culinart Arts Institute, 648.
Chaisalee, et al., Oct. 1, 2003, Mechanism of Antifoam Behavior of Solutions of Nonionic Surfactants Above the Cloud Point, Journal of Surfactants & Detergents, 6, No. 4, 345-351.
Chakraborty, et al., Jan. 1, 1972, Stabilization of Calcium Sensitive Plant Proteins by k-Carrageenan, Journal of Food Science, 37, 719-721.
Cheer, et al., Jan. 1, 1983, Effects of Sucrose on the Rheological Behavior of Wheat Starch Pastes, Journal of Applied Polymer Science, 28, 1829-1836.
Cox, et al., Jun. 20, 2007, Surface Properties of Class II Hydrophobins from *Trichoderma reesei* & Influence on bubble stability, Langmuir, 23, 7995-8002.
CRC, Jan. 1, 2008, Fennema's Food Chemistry, CRC Press, 4th Ed., pp. 727-728, Taylor & Francis Group.
Cruse, May 26, 1970, Whipped Soup is Tasty, St. Petersberg Independant, p. 1.
Damodaran, Oct. 27, 2004, Adsorbed layers formed from mixtures of proteins, Current Opinion to Colloid & Interface Science, 9, 328-339.
Davis, et al., Jan. 1, 2001, Application of foaming for the recovery of surfactin from *B. subtilis* ATCC 21332 cultures, Enzyme & Microbial Technology, 28, 346-354.
Dickinson, Dec. 2, 2010, Mixed biopolymers at interfaces: Competitive adsorption and multilayer structures, Food Hydrocolloids, 25, 1966-1983.
Dictionary.com, Jun. 14, 2010, Stabilizer, Dictionary.com, 1-4.
Fellows, 2000, Principles and Practice, Food processing technology, 2nd, 83, 140, 429, Foodhead Publishing.
Fox, 1992, Analytical methods for Milk Proteins, Advanced Dairy Chemistry 1: Proteins, 1, 1, 6-7.
Goh, Apr. 8, 2002, Applications and Uses of Palm and Palm Kernel Oils, Malaysian Oil Science and Technology, 11, 46-50.
Graham et al, Jul. 3, 1979, Proteins at Liquid Interfaces, Journal of Colloid and Interface Science, 70, 415-426.
Grant, Jan. 1, 1987, Grant & Hackh's Chemical Dictionary, McGraw-Hill, 5th Ed, 212.
Guinee et al., 2004, Salt in Cheese: Physical, Chemical and Biological Aspects, Cheese: Chemistry, Physics and Microbiology, vol. 1, 3rd ed., pp. 207-259.
Guner, et al., Jan. 1, 2007, Production of yogurt ice cream at different acidity, Intl Journ of Food Sc & Tech, 42, 948-952.
Holmes, et al., Oct. 10, 2006, Evaluation of antifoams in the expression of a recombinant FC fusion protein in shake flask cultures, Microbial Cell Factories, 5, No. 1, p. 30.
Hui, Jan. 1, 1992, Encyclopedia of Food Science & Tehcnology, John Wiley & Sons, 1, 204-210.
Hung, et al., Aug. 20, 2007, Cloud-point extraction of selected polycyclic aromatic hydrocarbons by nonionic surfactants, Separation & Purification Tech, 57, 1-10.
Katzbauer et al, Jun. 19, 1997, Properties and applications of xanthan gum, Polymer Degradation and Stability, vol. 59, 81-84, Elsevier.
Kilcast et al., Jun. 20, 2002, Sensory perception of creaminess and its relationship with food structure, Food Quality and Preference, 13, 609-623.
Kinderlerer, 1997, *Chrysosporium* species, potential spoilage organisms of chocolate, Journal of Applied Microbiology, vol. 83, pp. 771-778.
Kloek, et al., Feb. 2, 2001, Effect of Bulk and Interfacial Rheological Properties on Bubble Dissolution, Journal of Colloid & Interface Sc, 237, 158-166.
Kododziejcxzyk, Nov. 16, 2009, Adsortion of different proteins to Teflon sheets: Experimental Results, Nestle Research Center, 1-10.
Lambou et al., 1973, Whey Solids as Agricultural Foam Stabilizers, Jr. of Agr. and Food Chemistry, 21 No. 2, 257-263.
Linder, et al., Jul. 1, 2001, The hydrophobins HFBI & HFBII from *Trichoderma reesei* showing efficient interatctions w nonionic surfactants in aqueous two-phase sys, Biomacromolecules, 2, No. 2, 511-517.
Lumsdon, et al., Sep. 1, 2005, Adsorption of hydrophobin proteins at hydrophobic & hydrophilic interfaces, Colloids & Surfaces, 44, 172-178.
Marshall, Jan. 1, 2003, Ice Cream, Springer, 6th Ed, 70-73.
Martin, et al., Jan. 14, 2000, Sc30 Hydrophobin Organization in Aqueous Media & Assembly onto Surfaces as Mediated by Assoc Polysaccharide Schizophyllan, Biomacromolecules, 1, 49-60.
Mathlouthi, et al., Jan. 1, 1995, Rheological properties of sucrose solutions and suspensions, Sucrose Properties & Applic, pp. 126-154.
McCabe, et al., Dec. 1, 1999, Secretion of Cryparin a Fungal Hydrophobin, Applied & Environmental Microbiology, 65, No. 12, 5431-5435.
McGregor, et al., Jan. 1, 1988, Antifoam effects on ultrafiltration, Biotechnology & Bioengineering, 31, No. 4, 385-389.

\* cited by examiner

HYDROPHOBIN SOLUTION CONTAINING ANTIFOAM

TECHNICAL FIELD OF THE INVENTION

The present invention relates to a hydrophobin solution containing antifoam. In particular it relates to a hydrophobin solution containing antifoam obtained through a fermentation process.

BACKGROUND TO THE INVENTION

Foaming is a common problem in aerobic, submerged fermentations. Foaming is caused by the sparging of gas into the fermentation medium for the purpose of providing oxygen for the growth of the aerobic organism being cultivated (e.g. bacteria, yeasts, fungi, algae, cell cultures). If the fermentation medium contains surface active components such as proteins, polysaccharides or fatty acids, then foam can be formed on the surface of the medium as the sparged gas bubbles disengage from the liquid. Foaming creates a number of problems including the undesirable stripping of product, nutrients, and cells into the foam, and can make process containment difficult. A known method for controlling foaming is to use antifoams, of which several types are commonly used: silicone-based (e.g. polydimethylsiloxanes), polyalkylene glycols (e.g. polypropylene glycol), fatty acids, polyesters and natural oils (e.g. linseed oil, soybean oil). Antifoams replace foam-forming components on bubble surfaces, resulting in destruction of the foam by bubble coalescence. Antifoams are added at the start of and/or during the fermentation.

When the fermentation product is intended for use in foods, personal products or medicine, it is highly desirable that the product is excreted by the producing organism into the fermentation medium (i.e. extra-cellular, rather than intra-cellular production). This avoids the need to disrupt the cells by physical or chemical means in order to release the product for recovery. By maintaining the cells intact, the cellular material can be easily separated from the product so that it is free of intracellular and genetic material which is usually regarded as an undesirable contaminant. This can be especially important when the producing organism has been genetically modified. However, extra-cellular production of a hydrophobin may intensify the degree of foaming in the fermenter. The use of antifoams presents a particular problem in the extra-cellular production of hydrophobin for two reasons: firstly the amount of antifoam required is increased because the hydrophobin itself contributes to foaming in the fermenter. Secondly, the antifoam must be substantially removed since the presence of antifoam together with the hydrophobin will impair the hydrophobin functionality.

Bailey et al, *Appl. Microbiol. Biotechnol.* 58 (2002) pp 721-727 disclose the production of hydrophobins HFB I and HFB II by the fermentation of transformants of *Trichoderma reesei*. An antifoam (Struktol J633) was used to prevent foaming and the hydrophobin was purified using aqueous two phase extraction.

It has now been found that a certain level of antifoam can be present in the hydrophobin solution while the hydrophobin retains at least part of its functionality. It is thus possible to have a hydrophobin solution containing antifoam, therefore simplifying its production process and leading to significant savings.

BRIEF DESCRIPTION OF THE INVENTION

It is the object of the present invention to provide an aqueous solution containing at least 300 mg/l of hydrophobin and at least 0.3 mg/l of antifoam, wherein the antifoam/hydrophobin weight ratio is below 0.2, preferably below 0.15, more preferably below 0.1.

Preferably, aqueous solution contains at least 0.5 mg/l of antifoam.

Preferably also, the hydrophobin is a class II hydrophobin, most preferably HFBI or HFBII from *Trichoderma reesei*.

Preferably also, the antifoam has a cloud point.

Preferably the aqueous solution is concentrated so that the antifoam/hydrophobin ratio remains below 0.2 but its hydrophobin content is above 1 g/l, preferably 10 g/l even more preferably 100 g/l.

DETAILED DESCRIPTION OF THE INVENTION

Unless defined otherwise, all technical and scientific terms used herein have the same meaning as commonly understood by one of ordinary skill in the art (e.g. in cell culture, molecular genetics, nucleic acid chemistry, hybridisation techniques and biochemistry). Standard techniques used for molecular and biochemical methods can be found in Sambrook et al., Molecular Cloning: A Laboratory Manual, $3^{rd}$ ed. (2001) Cold Spring Harbor Laboratory Press, Cold Spring Harbor, N.Y. and Ausubel et al., Short Protocols in Molecular Biology (1999) $4^{th}$ Ed, John Wiley & Sons, Inc.—and the full version entitled Current Protocols in Molecular Biology.

Hydrophobins

Hydrophobins can be obtained by culturing filamentous fungi such as hyphomycetes (e.g. *Trichoderma*, basidiomycetes and ascomycetes. Particularly preferred hosts are food grade organisms, such as *Cryphonectria parasitica* which secretes a hydrophobin termed cryparin (MacCabe and Van Alfen; 1999, App. Environ. Microbiol 65: 5431-5435). Similarly, surfactin can be obtained from *Bacillus subtilis* and glycolipids from e.g. *Pseudomonas aeruginosa, Rhodococcus erythropolis, Mycobacterium* species and *Torulopsis bombicola* (Desai and Banat, Microbiology and Molecular Biology Reviews, March 1997, pp 47-64).

In EP 1 623 631 we have previously found that hydrophobins allow the production of aqueous foams with excellent stability to disproportionation and coalescence. Because hydrophobins are highly effective foaming agents, their presence in the fermentation medium presents a particular challenge for foam control.

Hydrophobins are a well-defined class of proteins (Wessels, 1997, Adv. Microb. Physio. 38: 1-45; Wosten, 2001, Annu Rev. Microbiol. 55: 625-646) capable of self-assembly at a hydrophobic/hydrophilic interface, and having a conserved sequence:

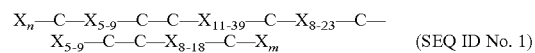

(SEQ ID No. 1)

where X represents any amino acid, and n and m independently represent an integer. Typically, a hydrophobia has a length of up to 125 amino acids. The cysteine residues (C) in the conserved sequence are part of disulphide bridges. In the context of the present invention, the term hydrophobia has a wider meaning to include functionally equivalent proteins still displaying the characteristic of self-assembly at a hydrophobic-hydrophilic interface resulting in a protein film, such as proteins comprising the sequence:

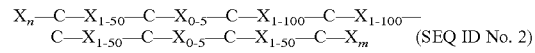

(SEQ ID No. 2)

or parts thereof still displaying the characteristic of self-assembly at a hydrophobic-hydrophilic interface resulting in a protein film. In accordance with the definition of the present invention, self-assembly can be detected by adsorbing the protein to Teflon and using Circular Dichroism to establish the presence of a secondary structure (in general, α-helix) (De Vocht et al., 1998, Biophys. J. 74: 2059-68).

The formation of a film can be established by incubating a Teflon sheet in the protein solution followed by at least three washes with water or buffer (Wosten et al., 1994, Embo. J. 13: 5848-54). The protein film can be visualised by any suitable method, such as labeling with a fluorescent marker or by the use of fluorescent antibodies, as is well established in the art. m and n typically have values ranging from 0 to 2000, but more usually m and n in total are less than 100 or 200. The definition of hydrophobin in the context of the present invention includes fusion proteins of a hydrophobin and another polypeptide as well as conjugates of hydrophobin and other molecules such as polysaccharides.

Hydrophobins identified to date are generally classed as either class I or class II. Both types have been identified in fungi as secreted proteins that self-assemble at hydrophobilic interfaces into amphipathic films. Assemblages of class I hydrophobins are generally relatively insoluble whereas those of class II hydrophobins readily dissolve in a variety of solvents. Preferably the hydrophobin is soluble in water, by which is meant that it is at least 0.1% soluble in water, preferably at least 0.5%. By at least 0.1% soluble is meant that no hydrophobin precipitates when 0.1 g of hydrophobin in 99.9 mL of water is subjected to 30,000 g centrifugation for 30 minutes at 20° C.

Hydrophobin-like proteins (e.g. "chaplins") have also been identified in filamentous bacteria, such as *Actinomycete* and *Streptomyces* sp. (WO01/74864; Talbot, 2003, Curr. Biol, 13: R696-R698). These bacterial proteins by contrast to fungal hydrophobins, may form only up to one disulphide bridge since they may have only two cysteine residues. Such proteins are an example of functional equivalents to hydrophobins having the consensus sequences shown in SEQ ID Nos. 1 and 2, and are within the scope of the present invention.

More than 34 genes coding for hydrophobins have been cloned, from over 16 fungal species (see for example WO96/41882 which gives the sequence of hydrophobins identified in *Agaricus bisporus*; and Wosten, 2001, Annu Rev. Microbiol. 55: 625-646). For the purpose of the invention hydrophobins possessing at least 80% identity at the amino acid level to a hydrophobin that naturally occurs are also embraced within the term "hydrophobins".

Antifoams

The term "antifoam" includes both antifoams which are usually added before foaming occurs and also those which are usually added once the foam has formed (sometimes known as defoamers). A definition of antifoams used in the present invention is found in "Foam and its mitigation in fermentation systems"—Beth Junker—Biotechnology Progress, 2007, 23, 768-784

A specific group of antifoams suitable for use in the present invention are those that exhibit a cloud point. The cloud point is the temperature at which an aqueous solution of the antifoam becomes visibly turbid as it phase separates (i.e. the antifoam molecules form aggregates which scatter light) as described on p63 of *Surfactant Aggregation and Adsorption at Interfaces*, J. Eastoe, in *Colloid Science: Principles, Methods and Applications*, ed. T. Cosgrove, Blackwell Publishing, 2005.

Examples of antifoams which display cloud points include poly(alkylene glycol) (PAG) based compounds such as ethylene oxide/propylene oxide block co-polymers, polyalcohols based on ethylene oxide/propylene oxide block copolymers and polyethers of ethylene and propylene oxides; and fatty acid ester-based compounds.

The cloud point depends on the surfactant composition and chemical structure. For example, for polyoxyethylene (PEO) non-ionic surfactants, the cloud point increases as the EO content increases for a given hydrophobic group. Preferably the cloud point of the antifoam is between 0° C. and 90° C., more preferably between 5° C. and 60° C.

Preferably, the antifoam comprises at least one non-ionic surfactant/polymer, such as a polyether, a poly(alkylene glycol), an ethylene/propylene oxide block co-polymer, a polyalcohol based on an ethylene/propylene oxide block co-polymer, a polypropylene glycol-based polyether dispersion, or an alkoxylated fatty acid ester. PAG-based antifoams (such as Struktol J647 obtainable from Schill and Seilacher), polyalcohols based on EO/PO block co-polymers (such as Struktol J647 obtainable from Schill and Seilacher) and other non-ionic surfactant antifoams are particularly effective at destroying foam, even in the presence of powerful foaming agents such as hydrophobin.

Mixtures of antifoams can be used, in which case, the cloud point of such a mixture is defined as the highest cloud point of the individual components.

Some common commercially available antifoams that exhibit a cloud point are shown in Table 1.

TABLE 1

| Antifoam | Cloud Point/° C. |
|---|---|
| Poly(alkylene glycol) | |
| Struktol J647, Schill & Seilacher | 24 |
| Struktol SB2121 | ca. 30 |
| UCON LB 65, Dow Chemical Company | 25 |
| UCON LB 285 | 15 |
| UCON LB 625 | 10 |
| UCON LB 1715 | 8 |
| KFO673, Lubrizol | 25 |
| ST934, Pennwhite Ltd | ca. 20 |
| Ethylene/propylene oxide block copolymers | |
| Pluronic PE3100, BASF | 41 |
| Pluronic PE6100 | 23 |
| Pluronic PE6200 | 33 |
| Pluronic PE8100 | 36 |
| Pluronic PE10100 | 35 |
| Mazu DF204, BASF | 18-21 |
| Polyalcohol based on EO/PO block copolymer | |
| Struktol J650, Schill & Seilacher | 13 |
| Polypropylene glycol based polyether dispersions | |
| Antifoam 204, Sigma | 15 |
| Alkoxylated fatty acid ester | |
| Struktol J673, Schill & Seilacher | 30 |

Antifoam Measurement Method

The concentrations of the antifoam in the filtrates were determined by using the Lange LCK 433 Water Testing Kit for non-ionic surfactants. This uses the principle that non-ionic surfactants (such as J647) form complexes with the indicator TBPE (tetrabromophenolphthalein ethyl ester), which can be extracted in dichloromethane and photometrically measured to determine the concentration. First, a calibration curve was constructed. A 0.3% (w/v) solution of Struktol J647 was prepared by taking an aliquot of 3.00 g Struktol J647 and diluting to 1 L with MilliQ water at 15° C. Aliquots were taken from this and diluted with MilliQ water to give concentrations of: 6, 15, 30, 60, 150 and 300 mg/L. MilliQ water was used as a blank sample. 0.2 ml samples of each concentration were added to the kit test tubes containing TBPE and dichloromethane. The tubes were gently mixed for 2 minutes and allowed to stand for 30 minutes. They were then measured in a Lange DR2800 spectrophotometer in at 605 nm in accordance with the Testing Kit instructions.

The filtrates were then diluted 1/10 with MilliQ water. 0.2 ml samples were measured in the spectrophotometer as before, and the concentration of the antifoam in each filtrate was read off from the calibration graph. The amount (%) of antifoam remaining in the filtrate was calculated as (measured concentration in filtrate)/(known starting concentration)×100%.

Antifoam concentrations down to 0.2 mg/L ($2\times10^{-5}$% w/v) can be measured by a similar technique, using the Lange LCK 333 Water Testing Kit, and constructing a calibration curve in the appropriate concentration range. In this case a 2 ml aliquot of the sample to be measured is added to the test kit, rather than 0.2 ml.

Fermentation Process and Removal of the Antifoam

The fermentation to produce the foaming agent is carried out by culturing the host cell in a liquid fermentation medium within a bioreactor (e.g. an industrial fermenter). The composition of the medium (e.g. nutrients, carbon source etc.), temperature and pH are chosen to provide appropriate conditions for growth of the culture and/or production of the foaming agent. Air or oxygen-enriched air is normally sparged into the medium to provide oxygen for respiration of the culture.

The antifoam may be included in the initial medium composition and/or added as required through the period of the fermentation. Common practice is to employ a foam detection method, such as a conductivity probe, which automatically triggers addition of the antifoam. In the present invention, the antifoam is preferably present at a final concentration of from 0.1 to 20 g/L, more preferably from 1 to 10 g/L.

The fermenter temperature during step i), i.e. during fermentation, may be above or below the cloud point of the antifoam. Preferably the fermenter temperature is above the cloud point of the antifoam, since the antifoam is most effective at causing bubble coalescence and foam collapse above its cloud point. The fermenter temperature is generally chosen to achieve optimum conditions for growth of the host cells and/or production.

At the end of the fermentation, the antifoam must be substantially removed to ensure that the functionality of the foaming agent is not impaired. Removal of the antifoam is achieved by ensuring that the temperature of the fermentation medium is above the cloud point of the antifoam, so that the antifoam phase separates. The phase separated antifoam can be removed from the fermentation medium by any suitable method such as:

filtration, e.g. dead-end filtration or a filter press
  membrane (cross-flow) filtration, e.g. microfiltration or ultrafiltration
  centrifugation
  adsorption, using e.g. activated carbon, silica or diatomaceous earth as an absorbent.

More antifoam is removed if the temperature of the fermentation medium is at least 10° C. above the cloud point, preferably at least 20° C. above the cloud point, most preferably at least 30° C. above the cloud point. Preferably the temperature of the fermentation medium is less than 90° C., more preferably less than 75° C. In a preferred embodiment, the antifoam has a cloud point in the range 20-30° C. and the temperature of the fermentation medium is in the range 40-60° C.

A preferred method for separating the antifoam is membrane filtration. It has been generally thought that carrying out membrane filtration of fermentation broths containing an antifoam at temperatures above its cloud point results in fouling of the membrane by the precipitated antifoam, causing a low permeate flux and consequent processing difficulties: see for example Yamagiwa et al., *J. Chem. Eng. Japan,* 26 (1993) pp 13-18, and WO 01/014521. Thus it has previously been thought that membrane filtration should take place at temperatures below the cloud point. However, acceptable fluxes are obtained when carrying out ultrafiltration and microfiltration operations at a temperature of about 25° C. above the cloud point of the antifoam.

In order to ensure that the product foaming agent is free from of intracellular and genetic material (which is usually regarded as an undesirable contaminant) the cells must be removed from the fermentation medium. In a preferred embodiment, the cells are separated from the medium at the same time as the precipitated antifoam is removed, for example in a microfiltration step which takes place at a temperature above the cloud point.

In an alternative embodiment the cells may be removed from the medium in a separate step prior to the removal of the antifoam—for example by filtration (e.g. dead-end filtration or a filter press), membrane/cross-flow filtration, (e.g. microfiltration or ultrafiltration), or centrifugation—at a temperature below the cloud point. In this embodiment, a purification and/or concentration step (e.g. by ultrafiltration) may be carried out (again at a temperature below the cloud point) after cell removal but before antifoam separation. The medium is then heated to a temperature above the cloud point so that the antifoam can be removed as already described.

Once the antifoam and the cells have been removed from the fermentation medium, the product foaming agent may be further purified and concentrated as required, e.g. by ultrafiltration. If the foaming agent is a hydrophobin, it can be purified from the fermentation medium by, for example, the procedure described in WO01/57076 which involves adsorbing the hydrophobin to a surface and then contacting the surface with a surfactant, such as Tween 20, to elute the hydrophobin from the surface. See also Cohen et al., 2002, Biochim Biophys Acta. 1569: 139-50; Calonje et al., 2002, Can. J. Microbiol. 48: 1030-4; Askolin et al., 2001, Appl Microbiol Biotechnol. 57: 124-30; and De Vries et al., 1999, Eur J Biochem. 262: 377-85.

The present invention will now be further described with reference to the following examples which are illustrative only and non-limiting.

Example 1

Removal of Antifoam From a Fermentation Liquor Containing a Foaming Agent

A fed-batch fermentation of a genetically modified strain of *Saccharomyces cerevisiae* was performed. The strain had been modified by incorporating the gene encoding the hydrophobin HFBII from the fungus *Trichoderma reesei* (a foaming agent) in such a way that extracellular expression of the hydrophobin was achieved during fermentation. Fermentation was carried out essentially as described by van de Laar T of al., in *Biotechnol Bioeng.* 96(3):483-94 (1997), using glucose as a carbon source and scaling the process to a total volume of 150 L in a 300 L fermentation vessel. The antifoam Struktol J647 was used to control foaming during the fermentation (instead of Struktol J673 used by van de Laar T et al).

At the end of the fermentation, the fermentation liquor was microfiltered at 15° C. (i.e. below the cloud point of the antifoam J647) to remove the yeast cells. Microfiltration was performed on pilot scale plant with Kerasep ceramic membranes having a pore size of 0.1 μm, using two volumes of diafiltration with deionised water. The liquor was then ultrafiltered, again at 15° C., to partially purify the HFBII. Ultrafiltration was by 1 kD Synder spiral wound polymeric membranes at a transmembrane pressure of 0.9 bar and four volumes of diafiltration.

The concentration of the antifoam in the fermentation liquor after the ultrafiltration step was measured to be 0.196 g/L. The concentration of HFBII was measured to be 0.320 g/L by high performance liquid chromatography (HPLC), as follows. The sample was diluted with 60% aqueous ethanol to give an approximate concentration of 200 μg/ml prior to analysis. HPLC separation was performed on a Vydac Protein C4 column (250×4.6 mm) at 30° C. Hydrophobin was measured by UV detection at 214 nm and the concentration was calculated by comparison with samples of known HFBII concentration obtained from VTT Biotechnology (Espoo, Finland).

The cell-free liquor was then heated to 50° C., held at that temperature for 30 minutes, and filtered (0.2 μm pore size) to remove the antifoam. The remaining amounts of antifoam and HFBII in the filtrate were measured as before and are given in Table 2 (Stage 1). The filtrate from this first stage was then re-heated to 50° C., held at this temperature for a further 30 minutes, and filtered as before. The HFBII and antifoam concentrations in the resulting filtrate were measured and are also given in Table 2 (Stage 2).

TABLE 2

|  | Stage 1 | Stage 2 |
|---|---|---|
| Amount of HFBII in filtrate (g/L) | 0.32 | 0.30 |
| % of initial HFBII concentration remaining | 100% | 93.75% |
| Amount of antifoam in filtrate (g/L) | 0.05 | .028 |
| % of initial antifoam concentration remaining | 25.5% | 14.3% |
| Mass ratio antifoam:hydrophobin | 0.156 | 0.093 |

The resulting hydrophobin solution was found to have satisfactory foaming properties.

The various features and embodiments of the present invention, referred to in individual sections above apply, as appropriate, to other sections, mutatis mutandis. Consequently features specified in one section may be combined with features specified in other sections, as appropriate.

All publications mentioned in the above specification are herein incorporated by reference. Various modifications and variations of the described methods of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in the relevant fields are intended to be within the scope of the following claims.

The invention claimed is:

1. A composition for production of stable aqueous foams comprising at least 300 mg/l of hydrophobin and at least 0.3 mg/l of antifoam, wherein the antifoam/hydrophobin weight ratio is below 0.2; wherein the antifoam has a cloud point between 0° C. and 90° C. and wherein the antifoam is selected from a polyether, a olyoxyethylene polymer, a poly(alkylene glycol), an ethylene/propylene oxide block co-polymer, a polyalcohol based on an ethylene/propylene oxide block co-polymer, a polypropylene glycol-based polyether, an alkoxylated fatty acid ester or a blend thereof.

2. The composition according to claim 1 wherein the hydrophobin is a class II hydrophobin.

3. The composition according to claim 1 wherein the hydrophobin is HFBI or HFBII from *Trichoderma reesei*.

4. The composition according to claim 1 wherein the antifoam has a cloud point between 5° C. and 60° C.

5. The composition according to claim 1 containing at least 1 g/l of hydrophobin.

6. The composition of claim 1 wherein the antifoam/hydrophobin weight ratio is below 0.15.

7. The composition of claim 1 wherein the antifoam/hydrophobin weight ratio is below 0.1.

8. The composition of claim 1 wherein the antifoam/hydrophobin weight ratio is at least 10 g/1.

9. The composition of claim 1 wherein the antifoam/hydrophobin weight ratio is at least 100 g/l.

* * * * *